US007625844B1

(12) United States Patent
Yang et al.

(10) Patent No.: US 7,625,844 B1
(45) Date of Patent: Dec. 1, 2009

(54) METHOD FOR SCREENING ANTI-ADHERENT COMPOUNDS ON POLYMERS FOR PREVENTING BIOFILM FORMATION

(75) Inventors: Fan Yang, Oak Hill, VA (US); Guang Yang, Oak Hill, VA (US)

(73) Assignee: Biopath Laboratory Incorporated (Delaware), Reston, VA (US)

( * ) Notice: Subject to any disclaimer, the term of this patent is extended or adjusted under 35 U.S.C. 154(b) by 0 days.

(21) Appl. No.: 11/404,807

(22) Filed: Apr. 17, 2006

(51) Int. Cl.
  *C40B 30/06* (2006.01)
(52) U.S. Cl. .............................. 506/10; 506/18; 506/7; 435/7.2
(58) Field of Classification Search ....................... None
  See application file for complete search history.

(56) References Cited

OTHER PUBLICATIONS

Silen et al. 1998 Antimicrobial agents and chemotherapy 42:1447-1453.*
Poutrel et al. 1997 Clinical and Diagnostic Immunology 4:275-278.*
Fernandez-Lopez et al 2001 Nature 412:452-455.*
Fernandez-Lopez et al 2001 Nature 414:329 (correction).*
Costerton (1999 International J. Antimicrobial Agents 217:217-221.*
Yajko et al (1995 J. Clinical Microbiology 33:2324-2327).*
Kit S. Lam, "Application Of Combinatorial Library Methods In Cancer Research And Drug Discovery", Anti-Cancer Drug Design, 1997, 12, pp. 145-167.
Itzhak Ofek et al., "Anit-Adhesion Therapy Of Bacterial Diseases: Prospects and Problems", FEMS Immunology and Medical Microbiology, 38, 2003, pp. 181-191.
Kit S. Lam et al., "The "One-Bead-One-Compound" Combinatorial Library Method", Chem. Rev. 1997, 97, pp. 411-448.
X. Wang et al., "Applications Of Topologically Segregated Bilayer Beads In "One-Bead One-Compound" Combinatorial Libraries", J. Peptide Res. 2005, 65, pp. 130-138.
G. Dibdin, "Models For Studying Initial Adhesion And Surface Growth In Biofilm Formation On Surface", 1999 310, pp. 296-322.
Costerton, J.W. Introduction to biofilm. Int. J. Antimicrob Agents. 11(1999): 2217-2221.
Vinh DC, Embil JM. Device-related infections, a review. J Long Term Eff Med Implats, 15(2005): 467-88.

(Continued)

*Primary Examiner*—Christopher Low
*Assistant Examiner*—Christopher M. Gross
(74) *Attorney, Agent, or Firm*—Fei-Fei Chao; Andrews Kurth, LLP

(57) ABSTRACT

The instant invention provides a live labeling microorganism assay for screening a one-bead one-compound library to identify synthetic anti-adherent compounds for blocking biofilm formation. The compounds of libraries may be peptides, small molecules, nucleic acids, other types of molecules or a combination of the foregoing. The live labeling microorganisms are incubated with a one-bead one-compound library for a long period with fresh-labeled bacteria and nutrition replacement in regular intervals. Those beads without bacterial adhesion are transferred into nutritional agar for the culture. The true anti-adherent beads are isolated and the sequences of each isolated compound-bead are determined with sequencer. The anti-adherent compounds identified in this invention are proved to possess long-term effect of blocking bacterial adhesion and biofilm formation. Thus the instant invention provides a unique and powerful method to identify anti-adherent compounds from library more quickly and reliably than current state-of-the-art technology allows.

23 Claims, 6 Drawing Sheets
(5 of 6 Drawing Sheet(s) Filed in Color)

OTHER PUBLICATIONS

Schierholz JM, Beuth J, Rump A, Konig DP, Pulverer G. Novel strategies to prevent catheter-associated infections in oncology patients. J Chemother. 13, (2001): 239-50.

Dibdin G, Wimpenny J. Models for studying initial adhesion and surface growth in biofilm formation on surface, Methods Enzymol, 310 (1999): 296-322.

Poncin-Epaillard F, Legeay G. Surface engineering of biomaterials with plasma techniques. J Biomater Sci Polym Ed 14(2003): 1005-28.

Ofek, I., Hasty, D. L. & Sharon, N. Anti-adhesion therapy of bacterial diseases: Prospects and problems. FEMS Immunol Med Microbiol. 15 (2003): 181-191.

Lam, K. S., Salmon, S. E., Hersh, E. M. One-bead, one-peptide: a new type of synthetic peptide library for identifying ligand-binding activity. Nature 7 (1991): 82-84.

Lam, Kit S. "Application of combinatorial library methods in cancer research and drug discovery." Anti-Cancer Drug Design 12 (1997): 145-167.

Wang, X., Peng, L., Liu, R., Xu, B., Lam, K.S. Application of topologically segregated bi-layer beads in "one-bead one-compound" combinatorial libraries. J Pept Res 65 (1), 130-8, 2005.

* cited by examiner

Fluorescently live labeling bacteria
↓
Incubation of mix infection bacteria with one-bead one-compound (OBOC) library
↓
Replacement of incubation media with fresh labeling bacteria and nutrient every 2 days
↓
Harvesting compound-beads and rinsing them with sterile PBS
↓
Selection of anti-adherent compound-beads under fluorescent and light microscope
↓
Transferring beads that have no bacterial adhesion into LMP-BHI agar for the culture
↓
Identification of true anti-adherent compound-beads
↓
Determination of the chemical structures of the compounds by sequencer
↓
Re-syntheses of anti-adherent compound on beads in large quantities
↓
Confirmation of the anti-adherent efficacy using the invention method
↓
Re-syntheses of anti-adherent compound on polymer disks
↓
Determination of the anti-adherent spectrums using the invention method

*FIG. 1*

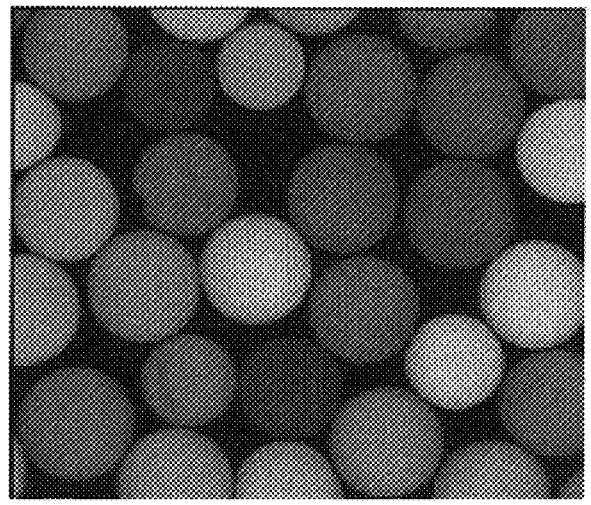
*FIG. 4*
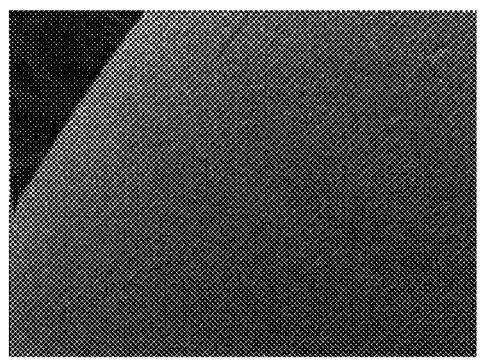 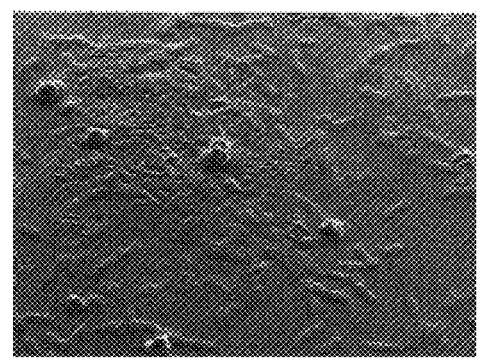
*FIG. 5A*  *FIG. 5B*

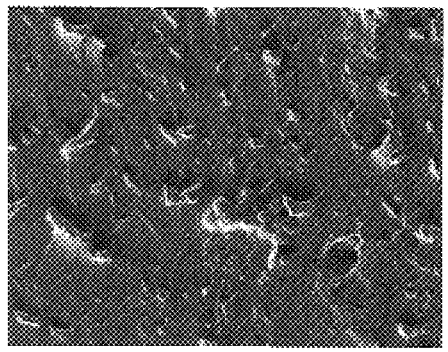 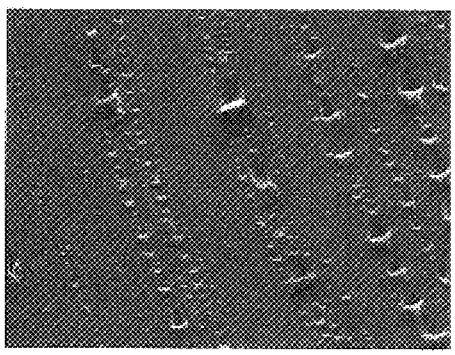
*FIG. 6A*  *FIG. 6B*
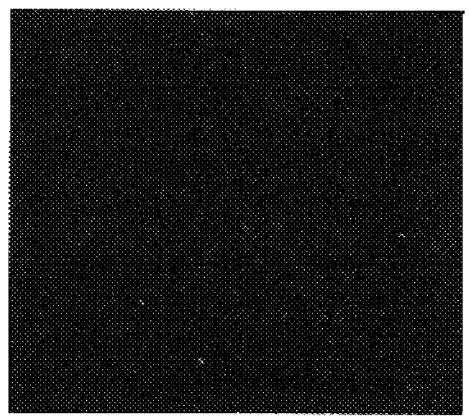 
*FIG. 7.1A*  *FIG. 7.1B*

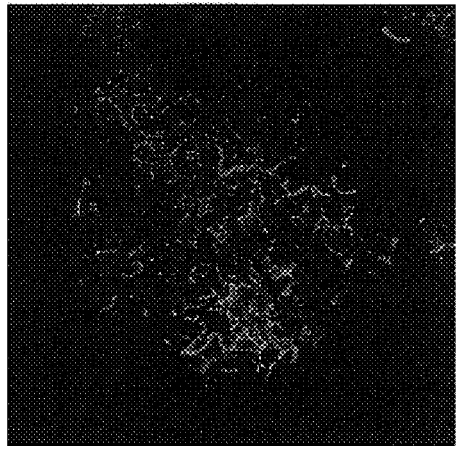 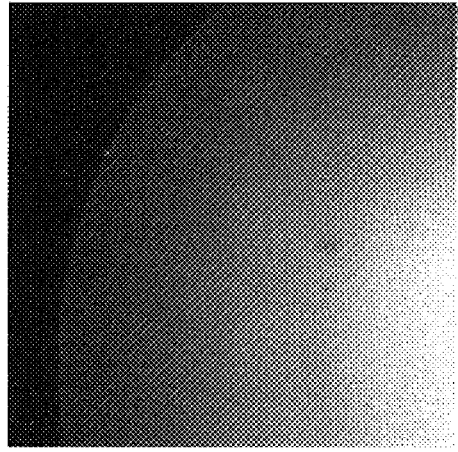
FIG. 7.2A    FIG. 7.2B
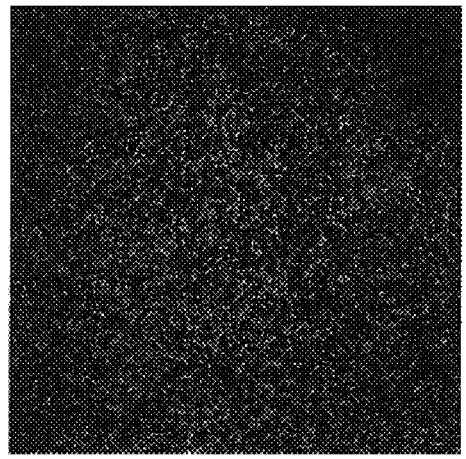 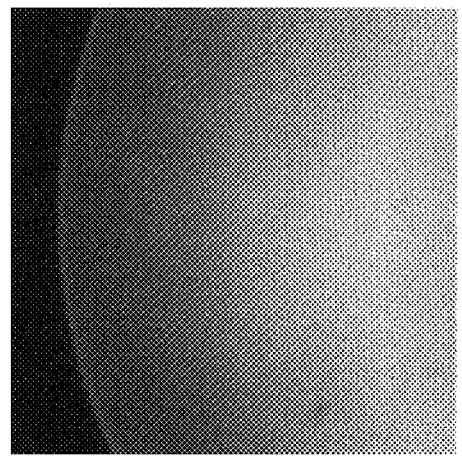
FIG. 7.3A    FIG. 7.3B

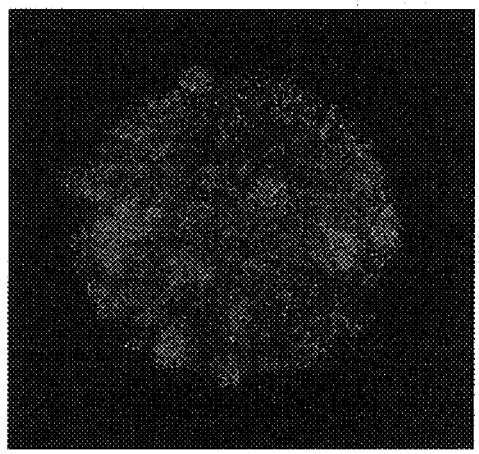
*FIG. 7.4A*
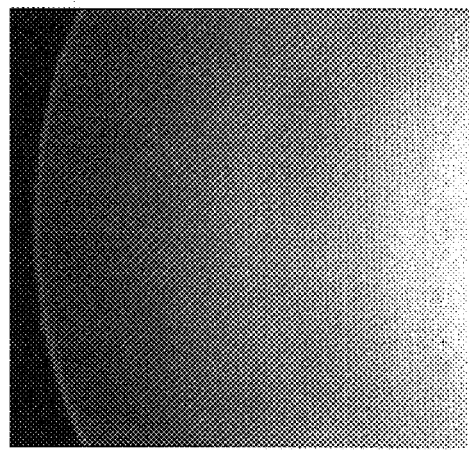
*FIG. 7.4B*
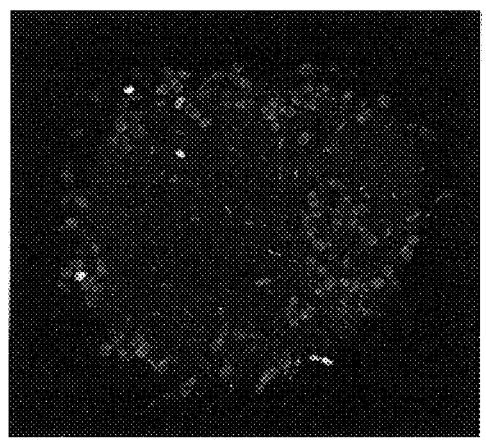
*FIG. 7.5A*
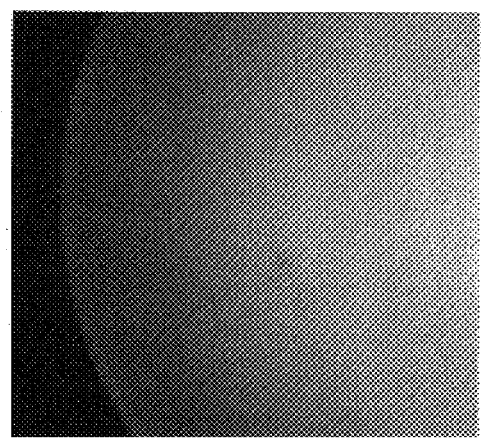
*FIG. 7.5B*

METHOD FOR SCREENING ANTI-ADHERENT COMPOUNDS ON POLYMERS FOR PREVENTING BIOFILM FORMATION

RELATED APPLICATION

The present invention claims the priority of U.S. Provisional Application No. 60/671,060, filed on Apr. 14, 2005, which is herein incorporated by reference.

FIELD OF THE INVENTION

The invention relates to screening methods of incubation of live labeling bacteria with one-bead one-compound library to identify long-term anti-adherent compounds for blocking biofilm formation. The invention also relates to the methods for examination and identification of the anti-adherent compounds under fluorescent and light microscopes as well as confocal laser scanning microscope.

BACKGROUND OF THE ANTI-ADHERENT STRATEGY

The research of anti-bacterial adhesion and its significance is a large field covering different aspects of nature and human life, such as marine science, soil and plant ecology, food industry and most importantly, the biomedical field. Implanted medical devices are of increasing importance in the practice of medicine and currently there are more than 100,000 products in over 1700 categories. It is estimated that more than 3-million people in the United States have long-term implants. However, bacterial adhesion and biofilm formation on medical devices are universal and challenging problems that can lead to complete failure of the implanted devices (Vinh et.al., 2005, J Long Term Eff Med Implants 15: 467-88). Adherence of bacteria to the surfaces of the polymer and subsequent biofilm formation play an important role in pathogenesis of device-related infection (Dibdin et.al., 1999, J. Methods Enzymol, 310: 296-322). Biofilm bacteria can usually survive the use of antiseptics and/or antibiotics at concentration 1000 to 1500 times higher than the concentrations needed to kill planktonic cells of the same species (Costerton, 1999, Int. J. Antimicrob. Agents, 11: 2217-2221). Current strategies for fighting biofilm formation focus on the coating biomaterial surfaces (Poncin-Epaillard, et.al., 2003, J. Biomater. Sci. Polym. Ed. 1005-28); and the incorporation of antimicrobial or antiseptic agents into current polymer biomaterials (Schierholz et, al., 2001, J. Chemother. 13: 239-50) with limited efficacy. So far, there appears to be a limited number of simple and reliable methods to detect anti-adherent efficacy and 'zero adhesion' has never been achieved.

An alternative approach for controlling bacterial adhesion is to select active molecules that can block bacterial adhesion, because the adhesion of microorganisms to the inert surfaces is the first step in the development of a wide variety of infections. Since anti-adherent agents are not bactericidal, the propagation and spread of resistant strains is much less likely to occur than as a result of exposure to bactericidal agents. The major drawback of anti-adhesion strategies is that most bacteria possess more than one type of adhesin. Adhesion may also involve factors other than just adhesion-receptor interactions such as hydrophobic and other non-specific interactions that occur under different shear-forces. For anti-adhesion therapy to be effective, either a single agent possessing a broad spectrum of anti-adherent activity, or multiple agents specifically inhibiting each type of adhesin should be applied to the infecting pathogens (Ofek et al. 2003, FEMS Immuno. Med. Microbiol. 15: 181-191).

"One-bead one-compound" (OBOC) combinatorial library concept (Lam, et al. 1991, Nature 354: 82-84) makes it convenient to identify a single agent against multiple adhesins and adherent factors by screening hundred to thousands of compounds with many bacterial strains in parallel. In this method, the library is prepared by a "split-mix synthesis" approach using polystyrene beads as a solid support. As a result, each bead displays only one chemical entity but there are approximately $10^{13}$ copies of the same chemical compound on and within one single bead. The exact chemical nature of the compound on selected bead can be determined through the usage of an automatic micro-sequencer. This technology has not only made an impact on the discovery of ligands for both known and unknown receptors on cancer cell lines, but also helped to accelerate the development of anti-cancer therapy (Lam et. al., 1997, Anti-Cancer Drug Design, 12:145-167).

BRIEF SUMMARY OF THE INVENTION

The invention is directed to the methods for screening a combinatorial library for the compounds that can block microbial adhesion and biofilm formation. The method comprises of introducing a suspension of live labeling *P. aeruginosa, S. epidermidis* and *S. aureus* to a combinatorial bead library made of cyclic peptides, or other types of molecules; incubating the labeled bacteria with the library for a long period with replacement of fresh labeled bacteria and nutrient in a regular intervals; isolating the beads having no bacterial adhesion; sterilizing and re-incubating isolated beads with *E. coli, K. pneumonia, E. faecalis, P. mirabilis, Bacillus* sp., *E. cloacae* and *C. albicans* for 14 days; and isolating the anti-adherent beads and determining the chemical structure of the compound grafted to that bead. The anti-adherent compounds are synthesized on disks according to the known sequences and re-incubated with fluorescently labeled bacteria for 14 days to confirm their anti-adherent efficacy. The anti-adherent compound grafting disks are proved to possess the properties of blocking bacterial adhesion, including *P. aeruginosa, S. epidermidis, S. aureus, E. coli, K. pneumonia, E. faecalis, P. mirabilis, Bacillus* sp., *E. cloacae* and *C. albicans* for at least 14 days.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1: Diagram depicting the steps of the identification of anti-adherent compound from a One-bead One-compound library.

FIG. 4: CLSM images of re-synthesized anti-adherent beads when exposed to *S. aureus*, *S. epidermidis*, and *P. aeruginosa* for 14 days, showing that there is no bacteria attachment or adhesion on any of these anti-adherent beads.

FIG. 5: Scanning electron microscope (SEM) showing that there is no bacterial adhesion on the anti-adherent disks (FIG. 5A), while *S. aureus*, *S. epidermidis* (coccid) and *P. aeruginosa* (rod) cells adhered and biofilm formation on the bared disks after 14-day incubation (FIG. 5B).

FIG. 6A and FIG. 6B: SEM images of *S. aureus*, *S. epidermidis* (coccid) and *P. aeruginosa* (rod) cells that adhered to roughly sliced bared disk after 14-days incubation (FIG. 6A), while there is no bacterial adhesion on the anti-adhesive disk (FIG. 6B).

FIG. 7.1A to FIG. 7.5B: CLSM images of anti-adherent spectrum when exposed to bacteria for 14-day, demonstrating that there are little of bacterial adhesion on peptide grafting disks, while a large number of bacterial adhesion and biofilm formation on the control disks. FIG. 7.1A (control) and FIG. 7.1B (peptide grafting disk) for *P. aeruginosa* and *S. epidermidis* mix incubation; FIG. 7.2A (control) and FIG. 7.2B (peptide grafting disk) for *K. pneumonia* and *E. faecalis* mix incubation; FIG. 7.3A (control) and FIG. 7.3 B (peptide grafting disk) for *E. coli* and *S. aureus* mix incubation, FIG. 7.4A (control) and FIG. 7.4B (peptide grafting disk) for *P. mirabilis* and *Bacillus*, sp. mix incubation; FIG. 7.5A (control) and FIG. 7.5B (peptide grafting disk) *C. albicans* and *E. clocacae* mix incubation.

DETAILED DESCRIPTION OF THE PREFERRED EMBODIMENT

Figure 2:
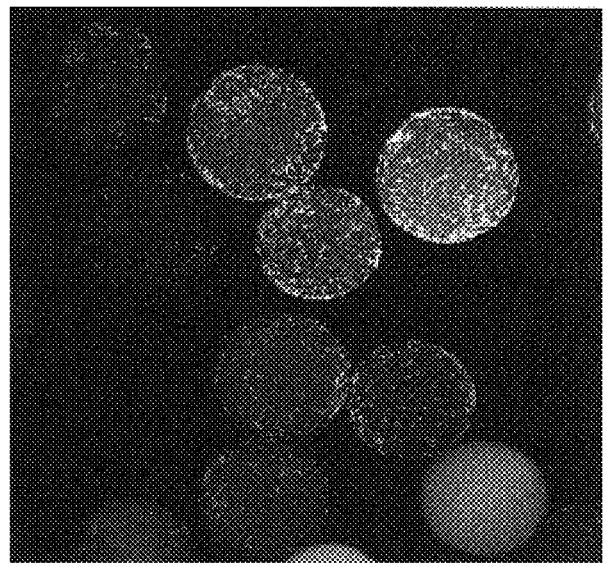
FIG. 2: Image of confocal laser scanning microscope (CLSM) of the compound-library incubation with *S. epidermidis, S. aureus* and *P. aeruginosa* for 14 days, in which a negative bead (no speckle on the surface) can easily be identified in a background of hundreds and thousands of positive beads (green and red speckles on the beads meaning mix bacterial adhesion, while green or red speckles only meaning single bacterial adhesion).

The embodiment of the invention includes a method, referred to as the live bacterial labeling assay, for screening a One-bead One-compound combinatorial library for the compounds that can block bacterial adhesion and consequently prevent biofilm formation as shown in FIG. 1. The methods of identification and isolation of anti-adherent compounds under light and fluorescent microscope are also described.

A One-bead One-compound combinatorial library is prepared using the 'split synthesis' approach described in Lam et al. (1991, Nature 354: 82-84). The compounds of the library may be peptides, small molecules, oligonucleotide, or other types of molecules. An example of a suitable library is a topographically segregated OBOC library is created according Wang et al with some modification (2005, J Pept Res 65 (1), 130-8). The library containing —NH—$X_1$—$X_2$—$X_3$—$X_4$—$X_5$—$X_6$—$X_7$—$X_8$-Cys (S—$CH_2$CO—)—$NH_2$—O, where "C" is D-cyctine, —NH is acetic acid pre-conjugated by nucleophilic attack of bromoacetic acid to the free thio group of the cysteine, which can react with amines (N-terminus) of peptides to generate thioether bridged cyclic peptides, X denote for D amino acids without arginine, histine and lysine. A suitable solid phase support, such as beads or discs made of polystyrene, agarose, acrylamide, glass, and plastics. Polystyrene beads have been found satisfactory. A standard synthetic solid phase peptide synthesis method, such as fluorenylmethyoxycarbonyl (Fmoc) chemistry and t-butyloxycarbonyl (Boc) chemistry are used. For the purposes of illustration, the combinatorial library referred to below is a cyclic peptide library, although it is understood that this is only one example of a library that can be used in this embodiment and that other libraries will also work.

Bacteria are prepared by inoculating the respective strains of gram positive and gram-negative bacteria onto nutrient agar slants (Difco) and stored at −70.degree. The stock bacteria are revived through the culturing of the respective bacteria from the nutrient agar slants. After 48 hours culturing, one colony of each strain is inoculated into brain heart infusion broth and cultured aerobically at 37.degree for 48 hours. Stationary phase of bacteria are collected by centrifugation at 5000 g for 10 minutes and labeled with the viability kit (Part #7005, Molecular Probes Inc., Eugene, Oreg.) consists of SYTO 9 at 1 µl/mL for gram negative bacteria and hexidium iodide at 1.2 µl/mL for gram positive bacteria in dark room at 37.degree for 15 minutes. The bacterial cells are collected by centrifugation and bacterial density is visually adjusted to equal that of 0.5 McFarland turbidity standard (approximately $10^8$ CFU/ml) using sterile 0.85% saline.

The suspension of bacteria is mixed with the 150,000 compound-library beads (the ratio of bacteria to peptide beads about 666:1) in culture media and incubated at 37 degree Celsius and 50 rpm with replacement of fresh-labeled bacteria and nutrient in regular intervals. After 14-day incubation, the beads are rinsed twice with sterile PBS and then observed under a fluorescent microscope (U-RFLT50, Olympus) and a light microscope. Those beads without bacterial adhesion (referred to as negative beads) are removed by a pipette. The negative beads are sterile and re-incubated with other species of bacteria to look for the broad spectrum of anti-adherent compounds. After long period incubation, those beads without bacterial adhesion are sorted and transferred into 0.4% low melting point brain heart infusion agar for the culture to detect the true negative beads. After removed from the agar plates-using pipette, negative beads are treated with 8 M guanidine hydrochloride for 10 minutes, rinsed with sterile water and transferred to a filter paper. The amino acid sequences of the anti-adherent compound on each isolated bead are then determined. This is preferably done with an automated protein sequencer, such as Procise 494 (Applied Biosystems, Foster City, Calif.).

Example of Method for Identification of Anti-Adherent Compounds from One-Bead One-Compound Library A One-bead One-peptide combinatorial library, containing random cyclic peptides, is prepared using the "split synthesis" method of Lam et al. A new type of synthetic peptide library contained $16^8=4.3\times10^9$ possible permutations of the compounds. The library containing the formula of "—NH—$X_1$—$X_2$—$X_3$—$X_4$—$X_5$—$X_6$—$X_7$—$X_8$-Cys (S—$CH_2$CO—)—$NH_2$—O", where "C" is D-cyctine, —NH is acetic acid pre-conjugated by nucleophilic attack of bromoacetic acid to the free thio group of the cysteine, which can react with amines (N-terminus) of peptides to generate thioether bridged cyclic peptides, X denote for D amino acids without arginine, histine and lysine. TentaGel™ polystyrene beads, with a diameter of 88 µm and 300 µm with grafted polyethylene glycol of 0.24 mml/g, are used as a solid phase support (Rapp Polymere, Germany). A synthetic solid phase method using fluoreylmethyoxycarbony (Fmoc) chemistry is adapted for synthesizing the cyclic peptide bead library. Gram-positive *S. epidermidis*, *S. aureus*, *E. faecalis*, *Bacillus*, sp and gram-negative *P. aeruginosa*, *E. coli*, *K. pneumonia*, *P. mirabilis*, *E. cloacae* as well as *C. albicans* are clinically isolated from vascular catheter. Bacterial cells are stocked on slant in −80 degree C. Bacteria are grown to stationary phase in brain heart infusion. Stationary phase of *S. epidermidis*, *S. aureus* and *P. aeruginosa* are collected by centrifugation at 5000 g for 10 minutes. The bacterial pallets are suspended in SYTO 9 at 1 µl /mL for gram-negative *P. aeruginosa*, and hexidium iodide at 1.2 µl/mL for gram-positive *S. epidermidis* and *S. aureus* in dark room at room temperature for 15 minutes. The cells are collected by centrifugation.

Bacterial density is visually adjusted to equal that of 0.5 McFarland turbidity standard (approximately $10^8$ CFU/ml) using sterile 0.85% saline and subsequently incubated with 0.2 ml (about 150,000 peptide beads) in 10 ml of brain heart infusion at 37 degree. Celsius and 50 rpm in a incubator in the dark room for 14 days with fresh fluorescent labeled bacteria nutrients replacement every 3 days.

At the end of the incubation, all of the beads are removed and rinsed with sterile PBS twice. A dissecting fluorescent microscope and light microscope are used to examine the beads (FIG. 2). Those beads without bacterial adhesion are isolated, sterilized with 75% alcohol and re-incubated with fluorescently labeled *E. coli, K. pneumonia, E. faecalis, P. mirabilis, Bacillus,* sp., *E. cloacae* and *C. albicans* at density of about $10^8$ CFU/ml brain heart infusions in the same situation as described above in the dark room for 14 days with fresh fluorescently labeled bacteria and nutrients replacement every three days. At the end of the incubation, the beads are rinsed with sterile PBS for twice and observed under a dissecting fluorescent microscope and light microscope. The negative beads are then transferred in to the low melting point brain heart infusion agar for the culture.

Figure 3:
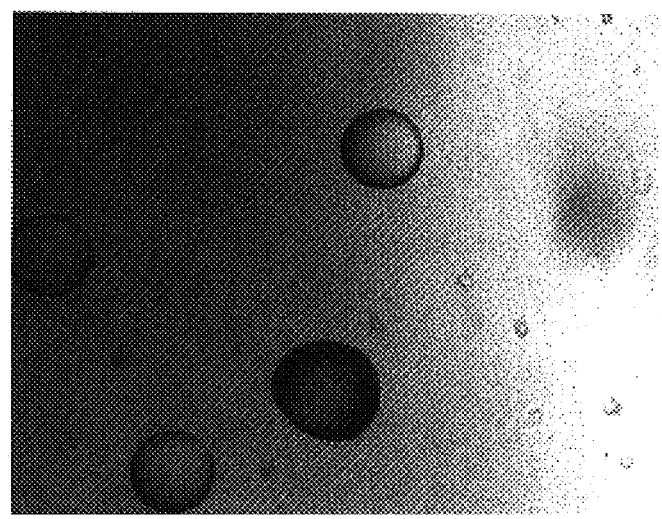
FIG. 3: Photomicrograph of anti-adherent beads isolated from 14-day incubation using fluorescently labeling screen assay and cultured in low melting point agar. Three of the beads in the field are true negative for bacterial adhesion, while the other one is positive with a bacterial layer growing around the bead, which is not recognized by fluorescent screening assay.

Each negative bead (FIG. 3) is isolated and removed from agar using micropipette and treated with 8 M guanidine hydrochloride for 10 minutes. The beads are then rinsed with sterile water for three times and transferred to a filter for the sequencing. The amino acid sequence of each isolated peptide bead is determined using an automated Procise 494 protein sequencer (Applied Biosystems, Foster City, Calif.)

These anti-adherent peptides are re-synthesized on beads in a large quantity, and re-incubated with the *S. epidermidis, S. aureus* and *P. aeruginosa* using the assay of the invention. The anti-adherent beads exhibit ability to block bacterial adhesion for at least 14 days (FIG. 4).

To confirm the anti-adherent properties and determine the anti-adherent spectrum on the flat surfaces, macro TentaGel™ beads are sliced into disk shape and the anti-adherent peptide is re-synthesized on the disks. The compound grafting disks are incubated with the fluorescently labeled bacteria for 14 days using the assay of the invention. The compound grafting disks exhibit the ability to block the bacterial adhesion and biofilm formation for at least 14 days (FIGS. 5, 6, 7).

What is claimed is:

1. A method for identifying an anti-adhesion compound comprising:
   generating a random one-bead one-compound (OBOC) library on solid supports to form a group of compound-bound OBOC library beads;
   labeling living microorganisms with a labeling agent to produce labeled living microorganisms;
   incubating said labeled living microorganisms with said group of compound-bound OBOC library beads in a liquid medium; and
   identifying from said group of compound-bound OBOC library beads an anti-adhesion compound-bound OBOC library bead characterized by having no microbial adhesion on said anti-adhesion compound-bound OBOC library bead by a fluorescent or light microscope;
   wherein said anti-adhesion compound is not bactericidal.

2. The method according to claim 1, wherein said anti-adhesion compound is a peptide, a nucleic acid, or a combination thereof.

3. The method according to claim 1, wherein said solid supports are agarose, acrylamide, glass, or plastic.

4. The method according to claim 1, wherein said solid supports are polystyrene beads.

5. The method according to claim 1, wherein said labeling agent is biotin, fluorophore, or a combination thereof.

6. The method according to claim 1, wherein said labeling agent is an enzyme.

7. The method according to claim 1, wherein said labeled living microorganisms comprise *Pseudomonas aeruginosa, Staphylococcus epidermidis, Staphylococcus aureus, Klebsiella pneumoniae, Enterococcus faecalis, Proteus mirabilis, Escherichia coli, Bacillus* sp., *Enterobacter cloacae, Candida albicans*, or any combination thereof.

8. The method according to claim 1, wherein said labeled living microorganisms are incubated with said compound-bound OBOC library beads at 37° C.

9. The method according to claim 1, wherein said labeled living microorganisms are incubated with said compound-bound OBOC library beads for about 14 days.

10. The method according to claim 1, wherein said anti-adhesion compound-bound OBOC library bead is isolated from said group of compound-bound OBOC library beads and the labeled living microorganisms by a pipette.

11. The method according to claim 1, wherein said liquid medium is a brain heart infusion culture medium.

12. The method according to claim 1, wherein said labeled living microorganisms are incubated with said compound-bound OBOC library beads under an aerobic condition.

13. The method according to claim 1, wherein said anti-adhesion compound-bound OBOC library bead is transferred into a low melting point brain heart infusion agar for further incubation to confirm that said anti-adhesion compound-bound OBOC library bead has no microorganism adhesion.

14. The method according to claim 2, wherein said peptide is a cyclic peptide.

15. The method according to claim 2, wherein said peptide is a linear peptide.

16. The method according to claim 15, further comprising a step of determining amino acid sequence of said anti-adhesion compound bound OBOC library beads.

17. The method according to claim 16, wherein said anti-adhesion compound bound OBOC library beads are treated with guanidine before determining said amino acid sequence of said anti-adhesion compound bound OBOC library beads.

18. The method according to claim 17, wherein said guanidine is 8 M guanidine.

19. The method according to claim 1, wherein said anti-adhesion compound prevents microbial adhesion and/or biofilm formation on an inert surface.

20. The method according to claim 1, wherein said incubation of said labeled living microorganisms with said group of compound-bound OBOC library beads in said liquid medium is repeated with different strains of said labeled living microorganisms to identify said anti-adhesion compound-bound OBOC bead with a broad spectrum of anti-adhesion activity.

21. The method according to claim 1, wherein said anti-adhesion compound is covalently grafted on and within said OBOC library bead.

22. The method according to claim 1, wherein said anti-adhesion compound is a small molecule.

23. The method according to claim 1, wherein said solid supports are polymer resins.

* * * * *